United States Patent
Kramer et al.

(10) Patent No.: US 10,420,739 B1
(45) Date of Patent: Sep. 24, 2019

(54) GLUTAURINE COMPOSITIONS AND THERAPEUTIC USES THEREOF

(71) Applicant: ThermoLife International, LLC, Phoenix, AZ (US)

(72) Inventors: Ronald Kramer, Phoenix, AZ (US); Alexander Nikolaidis, New Kallikratia (GR)

(73) Assignee: ThermoLife International, LLC, Phoenix, AZ (US)

( * ) Notice: Subject to any disclaimer, the term of this patent is extended or adjusted under 35 U.S.C. 154(b) by 0 days.

(21) Appl. No.: 13/917,045

(22) Filed: Jun. 13, 2013

(51) Int. Cl.
- *A61K 31/197* (2006.01)
- *A23L 1/305* (2006.01)
- *A61K 45/06* (2006.01)

(52) U.S. Cl.
CPC .......... *A61K 31/197* (2013.01); *A23L 1/3051* (2013.01); *A61K 45/06* (2013.01)

(58) Field of Classification Search
CPC ...... A61K 31/197; A61K 45/06; A23L 1/3051
See application file for complete search history.

(56) References Cited

U.S. PATENT DOCUMENTS 4,563,479 A * 1/1986 Feuer et al. .................. 514/562

OTHER PUBLICATIONS

DeMartino et al. Proc. Natl. Acad. Sci. USA vol. 75, No. 3, pp. 1369-1373, Mar. 1978.*
Baskin et al (Neuropeptides (1987) 9, 45-50).*
Hollingsworth et al. (Metabolism vol. 19, No. 11 (Nov. 1970).*
Balázs et al (Neuropeptides. (1988) vol. 12, Issue 2:55-58).*
Choksi et al (Birth Defects Research (Part B) 68:479-491 (2003)).*
Pilo et al (Am. J. Physiol. 258 (Endocrinol. Metab. 21): E715-E726,1990).*
Ann Barnes, Tex Heart Inst J. Jun. 2015; 42(3): 237-238 (Year: 2015).*
Bittner et al., Glutamyltaurine, Review Article; Amino Acids (2005) 28: 343-356, DOI 10.1007/s00726-005-0196-7; Published online Apr. 21, 2005; # Springer-Verlag 2005.

* cited by examiner

*Primary Examiner* — Angela C Brown-Pettigrew
(74) *Attorney, Agent, or Firm* — Booth Udall Fuller, PLC

(57) ABSTRACT

The present disclosure provides compositions and methods useful for the treatment of a body weight condition or a thyroid disorder. The compositions induces increased T3 levels while preventing thyroidal atrophy. Also provided are compositions and methods for the treatment of a disease or condition that is estrogen sensitive, estrogen receptor dependent or estrogen receptor mediated such as breast cancer.

7 Claims, No Drawings

GLUTAURINE COMPOSITIONS AND THERAPEUTIC USES THEREOF

TECHNICAL FIELD

The present disclosure relates to therapeutic compositions for the treatment of a body weight condition, a thyroid disorder, or a disease or condition that is estrogen sensitive, estrogen receptor dependent or estrogen receptor mediated.

BACKGROUND

The principal function of the thyroid gland is to produce the hormones thyroxine (tetraiodothyronine, T4) and tri-iodothyronine (T3), both of which play essential roles in regulating intermediary metabolism in virtually all tissues and in maturation of the nervous system, skeletal muscle and lungs in the developing fetus and the newborn (Werner and Ingbar, The Thyroid: A fundamental and clinical text (Braverman and Utiger, eds.) (1991) pp. 1-1362, Lippincott, Philadelphia; DeGroot, Endocrinology (DeGroot, ed.) (1995) Grune and Stratton, Orlando, Fla.). T3 and T4 are unique hormones in that both contain iodine as an essential constituent.

The hormone-producing thyroid follicular cells or thyrocytes display a highly specialized ability to transport iodide, the anionic form of iodine. This ability is an apparent cellular adaptation to sequester environmentally scarce iodine, thus ensuring adequate thyroid hormone production in most cases. Nevertheless, insufficient dietary supply of iodine is still prevalent among millions of people in many regions of the world, leading to endemic iodine deficiency disorders (IDD) often associated with lower-than-normal thyroid hormone production (Medeiros-Neto, et al., Thyroid Research, (Robbins and Braverman, eds.), (1976) p. 497, Excerpta Medica, Amsterdam).

Administering thyroidal compounds is a common way of treating thyroid disorders and can also increase metabolism, energy expenditure, and fat loss while promoting healthy weight and proportion of lean body mass to adipose tissue. A major disadvantage of thyroidal compounds such as T3,T4, and diiodothyronine is the atrophy they cause to the thyroid gland due to negative feedback. This results in the diminishing of their effectiveness over time as the body's endogenous production lowers. Compounds that increase T3 and T4 levels without causing thyroidal atrophy and compounds that can prevent or reverse thyroidal atrophy are desirable.

Estrogen is a steroid hormone that, while having important functions including the control of reproduction and the development of secondary sexual characteristics, also plays a predominant role in breast cancer growth and development. The use of estrogen for its positive effects can also detrimentally result in the stimulation of other tissues, such as those of the breast and uterus, and increase the risk of cancer at these sites.

The estrogen receptor (ER) is a member of a nuclear receptor superfamily consisting of orphan receptors and receptors for classic high-affinity ligands, such as steroid hormones, vitamin D, retinoids, and thyroid hormones. As a ligand inducible transcription factor, the estrogen receptor mediates the activity of endogenous estrogens in the development and function of the female reproductive system, the maintenance of bone mineral density, regulation of blood lipid profile, brain function, cardiovascular health and other physiologic processes. Endogenous estrogens include 17β-estradiol and estrones. ER has been found to have two isoforms, ER-α and ER-β.

Estrogen-Related Receptors (ERRs) are included in the nuclear receptor family and were the first orphan nuclear receptors found through a search for genes encoding proteins related to known nuclear receptors. While it was originally believed that the development and physiological roles of ERRs were quite distant from those of the classic ERs, it has recently been shown that in some cases ERRs can share target genes, coregulatory proteins, ligands, and sites of action with the ERs. See Riggs, L; Hartman, L, Selective Estrogen-Receptor Modulators—Mechanisms of Action and Application to Clinical Practice. *New England Journal of Medicine* 384:7, 2003. Like ER, ERRs are also implicated in breast cancer and other diseases. See Giguere, V, To ERR in the Estrogen Pathway. *Trends in Endocrinology & Metabolism*, 13:220, 2002.

Therapeutic agents that modulate endogenous levels of estrogens and thereby affect activation of the ER and ERRs are desirable to treat diseases that are estrogen sensitive, estrogen receptor dependent or estrogen receptor mediated. These diseases include cancer, obesity, stroke, hormonal disorders, lipid disorders, metabolic disorders, diabetes, osteoporosis, and heart disease.

SUMMARY

The present disclosure provides a method of treating a body weight condition comprising administering to a subject a composition comprising an effective amount of at least one compound selected from the group consisting of glutaurine, a salt of glutaurine, an ester of glutaurine, an isomer of glutaurine, and a functional derivative of glutaurine, thereby inducing weight and/or fat loss, preventing weight and/or fat gain, and/or increasing the metabolic consumption of adipose tissue in the subject.

In another aspect, the present disclosure provides a method of treating a disease or condition that is estrogen sensitive, estrogen receptor dependent or estrogen receptor mediated comprising administering to a subject a composition comprising an effective amount of at least one compound selected from the group consisting of glutaurine, a salt of glutaurine, an ester of glutaurine, an isomer of glutaurine, and a functional derivative of glutaurine, thereby inducing decreased endogenous levels of estrogen in the subject.

The present disclosure further provides a method of treating a thyroid disorder, comprising administering to a subject a composition comprising an effective amount of at least one compound selected from the group consisting of glutaurine, a salt of glutaurine, an ester of glutaurine, an isomer of glutaurine, and a functional derivative of glutaurine, thereby restoring normal thyroid function in the subject.

In one implementation, the present disclosure provides a method of increasing testosterone levels in a subject comprising administering to a subject a composition comprising an effective amount of at least one compound selected from the group consisting of glutaurine, a salt of glutaurine, an ester of glutaurine, an isomer of glutaurine, and a functional derivative of glutaurine, thereby inducing increased endogenous levels of testosterone in the subject.

DETAILED DESCRIPTION

As used herein, the verbs "comprise" and "include" as used in this description and in the claims and their conjugations are used in their non-limiting sense to mean that items following the words are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, the term "glutaurine" refers to a compound of the following structure:

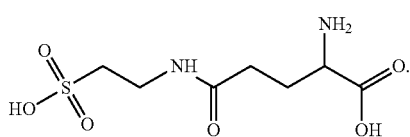 [SMILES: NC(CCC(=O)NCCS(=O)(=O)O)C(=O)O]

Synonymous terms of glutaurine include 5-L-glutamyl-taurine, g-L-glutamyltaurine, L-glutamine, N-(2-sulfoethyl)-N-(2-Sulfoethyl)-L-glutamine, N5-(2-Sulfoethyl)-L-glutamine, γ-glutamyltaurine, γ-L-glutamyltaurine, 5-glutamyltaurine, glutaurin, and Litoralon.

The term "salt of glutaurine" as used herein refers to a compound of the following formula:

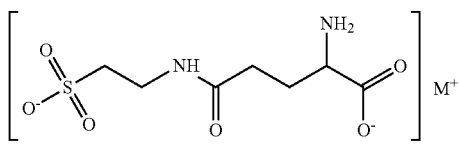

wherein M$^+$ is a positive counterion. In some implementations of the present disclosure, the salt of glutaurine contains an alkali metal or an alkaline earth metal. In certain aspects, the salt of glutaurine may be calcium glutaurinate or magnesium glutaurinate with the structures shown below. Magnesium glutaurinate may be particularly useful for the treatment of thyroid disorders or a body weight condition because of magnesium's beneficial effect on thyroidal function.

Calcium Glutaurinate:

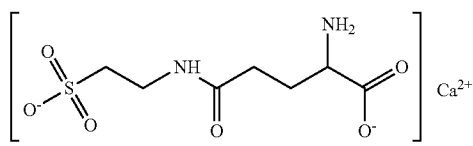

Magnesium Glutaurinate:

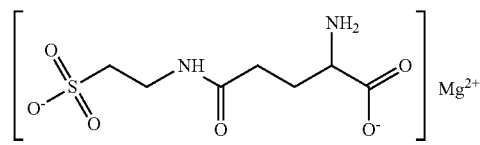

The term "ester of glutaurine" as used herein refers to derivatives of glutaurine with an ester linkage. A non-limiting example of an ester of glutaurine is glutaurine ethyl ester shown below. Other non-limiting examples are the methyl ester and the propionyl ester of glutaurine. An ester of glutaurine may exhibit slower but more long-lasting activity than glutaurine. Included within the term "ester of glutaurine" are salts of the esters such as magnesium diglutaurate ethyl ester.

Glutaurine Ethyl Ester:

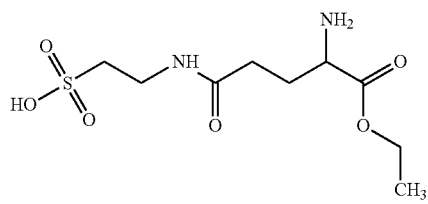 [SMILES: CCOC(=O)C(N)CCC(=O)NCCS(=O)(=O)O]

As used herein, the term "isomer of glutaurine" refers to a compound with the same molecular formula of glutaurine, $C_7H_{14}N_2O_6S$, but with a different structural formula. A non-limiting example of an isomer of glutaurine is α-glutaurine (aka alpha-glutamyl taurine and 4,7-diamino-5-oxo-6-sulfoheptanoic acid) shown below.

α-Glutaurine:

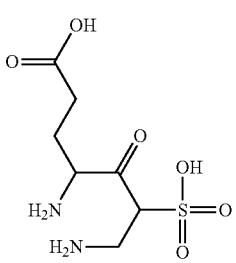 [SMILES: NCC(C(=O)C(N)CCC(=O)O)S(=O)(=O)O]

As used herein, a "functional derivative of glutaurine" is a derivative of glutaurine containing an acyl group or an alkyl group. In some implementations, the acyl or alkyl group may be linked to one of the amino groups on glutaurine. Functional derivatives of glutaurine include acetyl derivatives such as N1-acetylglutaurine, N2-acetylglutaurine, and N1, N2-diacetylglutaurine shown below. The acetyl derivatives of glutaurine exhibit lower potency but higher permeability across the blood brain barrier and a longer half-life. In certain aspects, the functional derivatives of glutaurine are alkylated amine derivatives such as N1-methyl-N2-dimethylglutaurine shown below. A functional derivative of glutaurine may also be an ester of glutaurine or a salt of glutaurine containing an acyl group or an alkyl group such as N1-methylglutaurine ethyl ester.

N1-Actelyglutaurine:

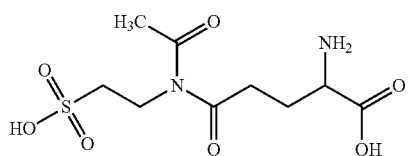 [SMILES: CC(=O)N(CCS(=O)(=O)O)C(=O)CCC(N)C(=O)O]

N2-Acetylglutaurine:

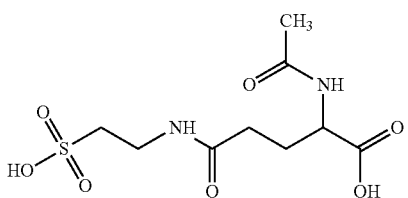 [SMILES: CC(=O)NC(CCC(=O)NCCS(=O)(=O)O)C(=O)O]

N1, N2-Diacetylglutaurine:

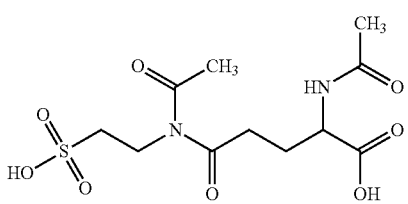 [SMILES: CC(=O)NC(CCC(=O)N(CCS(=O)(=O)O)C(C)=O)C(=O)O]

N1-Methyl-N2-Dimethylglutaurine:

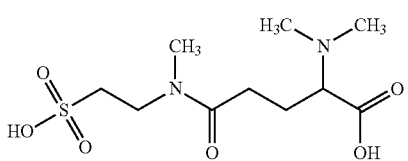

As used herein, an "effective amount," an "amount effective for," or "amount sufficient to" is defined as an amount effective, at dosages and for periods of time necessary, to achieve a desired biological result, such as reducing, preventing, or treating a disease or condition and/or inducing a particular beneficial effect. The effective amount of compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present disclosure may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

The present disclosure relates to the discovery that administration of a glutaurine compound increases T3 levels while decreasing estrogen levels in a subject. This effect on T3 and estrogen levels is observed with administration of surprisingly low amounts of the glutaurine compound. Because of the glutaurine compound's effect on T3 and estrogen levels it can be used to treat thyroid disorders, a body weight condition, and diseases or conditions that are estrogen sensitive, estrogen receptor dependent or estrogen receptor mediated such as breast cancer.

In one implementation, the present disclosure provides a method comprising administering to a subject regulating body weight at least one compound selected from the group consisting of glutaurine, a salt of glutaurine, an ester of glutaurine, an isomer of glutaurine, and a functional derivative of glutaurine in an amount effective to maintain muscle mass while inducing weight and/or fat loss, preventing weight and/or fat gain, and/or increasing the metabolic consumption of adipose tissue in the individual. The method may further comprise maintaining and/or inducing an increase in muscle mass. In one implementation, the composition may be administered to a subject in need thereof to treat obesity. In another implementation, the administration of the composition results in an increased energy expenditure and/or metabolism in the subject.

The retention of lean or muscle mass may be maintained selectively, in various regions of the body, e.g., in skeletal muscle, in the limbs (such as arms and legs) or the trunk. For example, the administration of the compound can maintain gastrocnemius muscle. Likewise, inducement of fat loss may also be selectively targeted in various regions or types, e.g., loss of fat pad mass, abdominal-fat, perirenal fat or subscapular fat and/or combinations. The present disclosure may also assist in inducing fat loss while maintaining lean or muscle mass. Maintaining muscle mass may include gaining at least about 1, 2, 5, or 10% muscle mass, or not losing any muscle mass, or losing no more than about 1%, 2%, or 5% of muscle mass during the period when the compound is administered to the subject.

The present disclosure also provides methods for treating a thyroid disorder in a subject such as hypothyroidism, hyperthyroidism, and thyroid cancer. The thyroid disorder may be associated with reduced or undetectable iodide transport activity in the subject's thyroid cells. The methods and compositions of the present disclosure may be used to support healthy thyroidal hormone levels and good thyroidal function.

In certain aspect, the compositions of the present disclosure induce an increase in T3 levels in a subject while preventing thyroidal atrophy. A negative feedback loop between the thyroid gland, the pituitary, and the hypothalamus maintains the endogenous thyroid hormones at a constant level in adults of higher vertebrates (Larsen P R (1989) Adv Exp Med Biol 261:11-26). Without wishing to be bound to any theory, the compositions of the present disclosure may stimulate T3 production without triggering this negative feedback loop, thus avoiding thyroidal atrophy.

In certain aspects, the compositions of the present disclosure can promote weight loss by increasing thyroidal production levels without negative effects on thyroidal function. The compositions can actually promote thyroid health and prevent other co-administered thyroidal compounds from causing thyroidal atrophy.

The compositions of the present disclosure may be used to treat any disease in which modulating one or more of estrogen levels, the ERs, the ERRs or a combination thereof treats the disease. In another aspect, the present disclosure provides compositions for the treatment of diseases or conditions that are estrogen sensitive, estrogen receptor dependent or estrogen receptor mediated.

In some implementations, the disease or condition may be breast cancer, ovarian cancer, colon cancer, prostate cancer, endometrial cancer, or uterine cancer. In other implementations, the disease or condition may be bone cancer, breast cancer, colorectal cancer, endometrial cancer, prostate cancer, ovarian cancer, uterine cancer, cervical cancer, lung cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, or infertility. Additional diseases that may be treated include proliferative disease, obesity, stroke, hormonal disorders, lipidemia and other lipid disorders, metabolic disorders, diabetes, diseases related to fetal development, osteoporosis and heart disease.

In certain aspects, the present disclosure provides a method of increasing testosterone in a subject comprising administering to a subject of a composition comprising at least one compound selected from the group consisting of glutaurine, a salt of glutaurine, an ester of glutaurine, an isomer of glutaurine, and a functional derivative of glutaurine induces increases endogenous levels of testosterone in the subject thereby inducing increased endogenous levels of testosterone in the subject. Administration of the composition may also induce decreased endogenous levels of estrogen in the subject.

Reducing estrogen levels in a subject generally results in increased testosterone levels. Grumbach and Auchus reported that estrogen deficiency in men leads to increased testosterone levels. See Grumbach and Auchus (1999) JCEM 84 (12): 4677. Furthermore, therapeutic agents that reduce estrogen levels commonly increase testosterone levels. Taxel et al. observed that men treated with the aromatase inhibitor, anastrozole, experienced a significant decrease in estradiol and an increase in total testosterone. See Taxel et al. (2001) JCEM 86 (6): 2869. Similarly, the compositions of the present disclosure have the effect of decreasing estrogen levels while increasing testosterone levels.

In some implementations, the effective amount of the compounds of the present disclosure is about 1 microgram (mcg) to about 7,500 mcg per day; e.g., any range within about 1 mcg to about 7,500 mcg per day such as about 100 mcg to about 3,000 mcg per day or about 500 mcg to about 1,500 mcg per day. In some implementations, the effective amount of the compounds is about 1 mcg per day, about 25 mcg per day, about 50 mcg per day, about 100 mcg per day, about 200 mcg per day, about 300 mcg per day, about 400 mcg per day, about 500 mcg per day, about 600 mcg per day, about 700 mcg per day, about 800 mcg per day, about 900 mcg per day, about 1,000 mcg per day, about 1,100 mcg per day, about 1,200 mcg per day, about 1,300 mcg per day, about 1,400 mcg per day, about 1,500 mcg per day, about 2,000 mcg per day, about 2,500 mcg per day, about 3,000 mcg per day, about 3,500 mcg per day, about 4,000 mcg per day, about 4,500 mcg per day, about 5,000 mcg per day, about 5,500 mcg per day, about 6,000 mcg per day, about 6,500 mcg per day, about 7,000 mcg per day, or about 7,500 mcg per day. As used herein, the term "about" refers to a +/−10% variation from the nominal value.

In some implementations, the compounds may be administered to a subject in an effective amount of about 1 mcg of compound per kg of body weight, about 2 mcg of compound per kg of body weight, about 3 mcg of compound per kg of body weight, about 4 mcg of compound per kg of body weight, about 5 mcg of compound per kg of body weight, about 6 mcg of compound per kg of body weight, about 7 mcg of compound per kg of body weight, about 8 mcg of compound per kg of body weight, about 9 mcg of compound per kg of body weight, about 10 mcg of compound per kg of body weight, about 11 mcg of compound per kg of body weight, about 12 mcg of compound per kg of body weight, about 13 mcg of compound per kg of body weight, about 14 mcg of compound per kg of body weight, or about 15 mcg of compound per kg of body weight. These dosages may be administered once a day, twice a day, three times a day, or more frequently if needed. When the dosages are administered more frequently throughout the day, it is contemplated that smaller dosages will generally be used than when a single administration is given in a day. In one implementation, the compounds are administered to a subject in an effective amount of about 10 mcg of compound per kg of body weight per day resulting in a dose of 0.75 mg/day for the average 75 kg human.

The composition of the present disclosure may further comprise at least one additional therapeutic agent selected from the group consisting of a thyroid hormone, an iodine compound, forskolin, 3,3'-diiodothyroacetic acid, and 3,5-diiodothyroacetic acid. The compositions are formulated appropriately for the intended use. For example, a pharmaceutical formulation for promoting weight loss in adults while maintaining healthy thyroid output includes:

100 mcg Thyroxine (T4);
1 mg Glutaurine; and
200 mcg Iodine (as Magnesium Iodide)

to be taken once daily preferably in the morning.

In another non-limiting example, a nutritional supplement formulation for promoting weight loss in humans while maintaining healthy thyroid output includes:

2000 mcg 3,3'-Diiodothyroacetic Acid;
2000 mcg 3,5-Diiodothyroacetic Acid;
0.5 mg Glutaurine; and
100 mg Forskolin to be taken once daily preferably in the morning.

In a non-limiting example, a pharmaceutical formulation for treating hypothyroidism includes:

100 mcg Thyroxine (T4) and
1 mg Glutaurine to be taken once daily.

In another non-limiting example, tablets consisting of 0.25 mg of glutaurine are to be taken as a nutritional supplement once or twice daily with food to promote overall thyroidal health.

Compositions for administration herein may form solutions, suspensions, tablets, pills, capsules, gel capsules, liquids sustained release formulations or powders. Compounds of the present disclosure can be administered to a subject in any suitable form using any suitable administration route. In various implementations, the compounds can be administered in a food composition, in a dietary supplement, in a pharmaceutical composition, in a nutraceutical composition, or as a medicament. Similarly, the compounds and compositions can be administered using a variety of administration routes, including oral, intranasal, intravenous, intramuscular, intragastric, transpyloric, subcutaneous, rectal, and the like.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents, and emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The compositions of the present disclosure may be formulated as nutritional or dietary supplements. The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

In one aspect, the compounds and compositions are administered to a subject in a dietary supplement. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the compounds or compositions and optional compounds such as vitamins, preservatives, probiotics, prebiotics, and antioxidants. This permits the supplement to be administered to a subject in small amounts, or in the alternative, can be diluted before administration to a subject. The dietary supplement may require admixing with a food composition or with water or other diluent prior to administration to the subject.

The dietary and nutritional supplements of the present disclosure may include a pharmaceutically acceptable additive. The additive may be a carrier, an excipient, a binder, a colorant, a flavoring agent, a preservative, a buffer, a dilutant, and/or combinations thereof.

Particular implementations of the compositions described herein may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

"Pharmaceutically acceptable" as used herein describes ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

For topical application the compounds can be administered in the form of an unguent, cream, ointment, lotion, solution or a patch. For parenteral administration, the compounds may be administered as injectable dosages or by continuous intravenous infusion of a solution, suspension or emulsion of the compound in a physiologically acceptable diluent as the pharmaceutical carrier, which can be a sterile liquid, such as water, alcohols, oils, emulsions, and other acceptable organic solvents, with or without the addition of a surfactant and other pharmaceutically acceptable adjuvants. The compounds can also be administered in the form of a depot injection or implant preparation, which may be formulated in such a manner as to permit a sustained release of the active ingredient.

Many methods of synthesis of glutaurine have been described. See, e.g., Bittner, S., et al., γ-L-glutamyltaurine, Amino Acids 28:343-356 (2005). Salts of glutaurine with alkali metals and alkaline earth metals may be produced by mixing glutaurine with the corresponding isomolar quantities of the appropriate alkali or alkaline earth base, such as magnesium hydroxide in a solution of an appropriate solvent, such as water or alcohol, and then removing the solvent from the mixture by drying under vacuum, for example.

Glutaurine ethyl ester may be produced by mixing glutaurine with an excess of alcohol, adding small quantities of $H_2SO_4$ or another strong acid and heating the mixture while stirring for about an hour. The mixture then is dried under vacuum and glutaurine ethyl ester is obtained.

N1, N2-diacetylglutaurine may be obtained by mixing glutaurine with an excess of acetyl chloride in the presence of pyridine. The mixture is refluxed for 2 hours and N1, N2-diacetylglutaurine is obtained after drying the mixture under vacuum.

N1-methyl-N2-dimethylglutaurine may be obtained by mixing glutaurine with an excess of methyl iodide ($CHI_3$). The mixture is then refluxed for 6 hours and N1-methyl-N2-dimethylglutaurine is obtained by drying the solution under vacuum.

This disclosure is further illustrated by the following additional examples that should not be construed as limiting. Those of skill in the art should, in light of the present disclosure, appreciate that many changes can be made to the specific implementations which are disclosed and still obtain a like or similar result without departing from the spirit and scope of the disclosure.

EXAMPLES

Example 1. Effects of Glutaurine on Thyroid Hormone and Estradiol Levels

To evaluate the effect of administration of glutaurine on estradiol and thyroid hormone levels in a human subject, approximately 800 micrograms (mcg) per day of glutaurine were administered orally to the subject over a period of about one month. At Day 0 prior to administration of the glutaurine and at Day 4 and Day 28 during administration of the glutaurine blood samples were collected and analyzed for the levels of estradiol, thyroid stimulating hormone (TSH), and the thyroid hormones triiodothyronine (T3) and thyroxine (T4). Total amounts of T3 and T4 were measured in the blood samples. Table 1 summarizes the levels of the hormones in the blood samples at each time point.

TABLE 1

Estradiol, TSH, T3, and T4 levels in blood samples collected prior to and during oral administration of glutaurine at approximately 800 mcg/day to a human subject.

|  | Estradiol (pg/mL) | TSH (mIU/L) | T4 (mcg/dL) | T3 (ng/dL) |
| --- | --- | --- | --- | --- |
| Day 0 | 36 | 3.01 | 8.3 | 91 |
| Day 4 | 32 | 3.28 | 7.9 | 96 |
| Day 28 | 30 | 2.74 | 7.3 | 109 |

Administration of glutaurine resulted in a marked decrease in estradiol levels and a consistent increase in T3 levels in the subject. T4 levels were slightly reduced after glutaurine administration, and no significant change was observed in TSH levels.

The subject reported that during administration of the glutaurine he experienced increased body temperature and increased sweating, which are indicative of rising energy expenditures and increased metabolism. The subject also reported fat loss as a result of the glutaurine administration.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present disclosure is not entitled to antedate such publication by virtue of prior invention.

It is understood that the disclosed implementations are not limited to the particular methodology, protocols and materials described as these can vary. It is also understood that the terminology used herein is for the purposes of describing particular implementations only and is not intended to limit the scope of the present disclosure which will be limited only by the appended claims.

Those skilled in the art will recognize, or be able to ascertain using no more than routine experimentation, many equivalents to the specific implementations described herein. Such equivalents are intended to be encompassed by the following claims.

What is claimed is:

1. A method of regulating body weight comprising administering about 500-1000 mcg per day of glutaurine to an obese human subject.

2. The method of claim 1, wherein administration of glutaurine increases levels of triiodothyronine (T3) in the subject while preventing thyroidal atrophy.

3. The method of claim 1, wherein the obese human subject is in need of inducing fat loss, preventing fat gain, and/or increasing metabolic consumption of adipose tissue to treat obesity.

4. The method of claim 1, wherein administration of glutaurine maintains muscle mass and/or induces an increase in muscle mass.

5. The method of claim 1, wherein the glutaurine is incorporated into a nutritional or dietary supplement.

6. The method of claim 1, wherein glutaurine is formulated in an orally administrable form selected from the group consisting of a tablet, a powder, a gel capsule, and a liquid.

7. The method of claim 1, wherein the glutaurine is administered in an amount effective for inducing fat loss, preventing fat gain, and/or increasing the metabolic consumption of adipose tissue in the obese human subject.

* * * * *